United States Patent [19]

Warren, III et al.

[11] Patent Number: 4,812,414

[45] Date of Patent: Mar. 14, 1989

[54] IMMUNOREACTIVE REAGENT PARTICLES HAVING TRACER, RECEPTOR MOLECULES AND PROTEIN OF PI LESS THAN 6

[75] Inventors: Harold C. Warren, III, Rush; Brian A. Snyder, Rochester, both of N.Y.

[73] Assignee: Eastman Kodak Company, Rochester, N.Y.

[21] Appl. No.: 98,250

[22] Filed: Sep. 18, 1987

[51] Int. Cl.$^4$ ................. G01N 33/546; G01N 33/547; G01N 33/569
[52] U.S. Cl. ........................................ 436/533; 435/7; 435/36; 436/534; 436/547; 436/825
[58] Field of Search ............... 436/533, 534, 547, 825; 435/36, 7

[56] References Cited

U.S. PATENT DOCUMENTS

| | | | |
|---|---|---|---|
| 4,307,190 | 12/1981 | Masson | 436/534 X |
| 4,459,361 | 7/1984 | Gefter | 436/523 |
| 4,560,504 | 12/1985 | Arnold | 260/112 |
| 4,591,571 | 5/1986 | Kuboyama et al. | 436/533 |
| 4,618,576 | 10/1986 | Rosenstein | 435/7 |
| 4,656,144 | 4/1987 | Hosaka | 436/534 |
| 4,677,080 | 6/1987 | Finkelstein | 436/534 |
| 4,713,350 | 12/1987 | Siegel | 436/534 X |

OTHER PUBLICATIONS

L. F. Fieser et al., "Advanced Organic Chemistry", p. 1048, Reinhold, New York, 1961.
Johnson et al., *Gene. Anal. Techn.* 1 (1984) pp. 3–8.

*Primary Examiner*—Sidney Marantz
*Attorney, Agent, or Firm*—J. Lanny Tucker

[57] ABSTRACT

A reagent useful in the determination of an immunoreactive species comprises water-insoluble particles having tracer molecules associated therewith. Bound to the outer surface of the particles are: (i) receptor molecules which are reactive with the species, and (ii) molecules of a protein having a pI less than about 6, and which protein is not reactive with either the species or the receptor molecules. The weight ratio of the receptor molecules to the low pI protein molecules is from about 100:1 to about 1:10. This reagent is useful in agglutination and other immunological reactions. A method of preparing the reagent includes providing a suspension of the particles and contacting them with the receptor molecules and low pI protein so as to attach both to the particles. The protein is present in the suspension in an amount such that substantially all of it is attached to the particles. The reagent thus prepared can be used, for example, in agglutination assays for the determination of a multivalent immunoreactive species, such as Streptococcus A antigen.

20 Claims, 1 Drawing Sheet

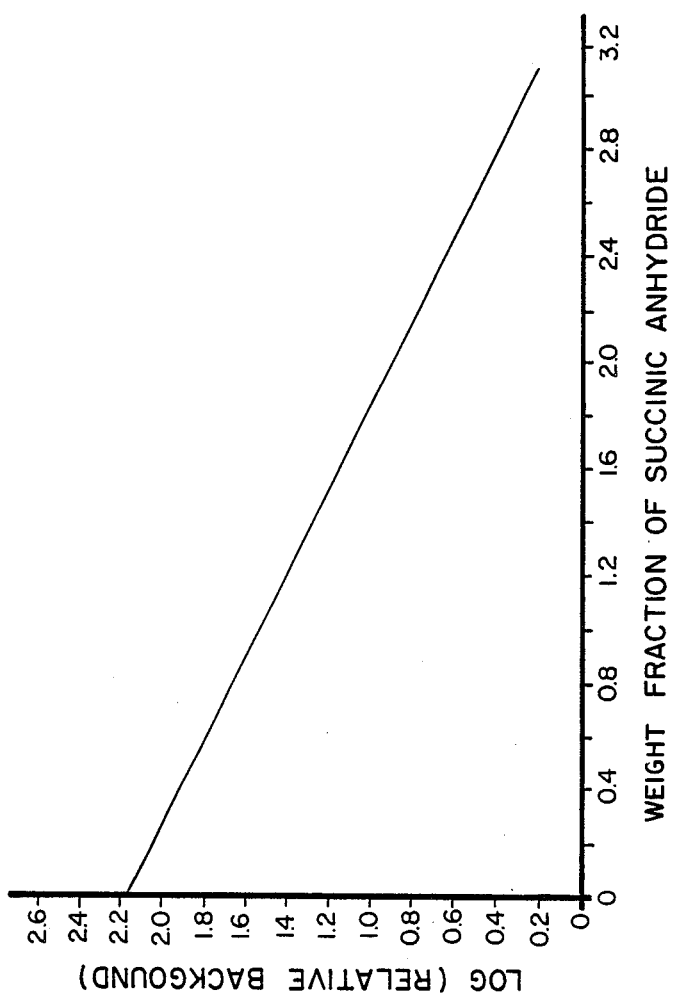

IMMUNOREACTIVE REAGENT PARTICLES HAVING TRACER, RECEPTOR MOLECULES AND PROTEIN OF PI LESS THAN 6

FIELD OF THE INVENTION

This invention relates to an immunoreactive reagent and a method of preparing it. It also relates to a method of using the reagent in an assay for an immunoreactive species, such as Streptococcus A antigen.

BACKGROUND OF THE INVENTION

The antigen-antibody reaction is the basis for all immunological test methods. Certain proteins known as antibodies are produced by mammals in response to the presence of an antigen, that is a foreign substance, which can be another protein or a carbohydrate. This normal body response to a foreign substance has led to the development of a number of techniques which are used to diagnose various diseases, disorders and physiological conditions. In a general sense, the component of an immunochemical reaction to be detected is defined herein as the immunoreactive species while the corresponding component reactive with the species is considered the receptor.

For example, in vitro tests for the presence of a suspected protein, antigen or antibody in a biological sample are carried out by adding an immunological counterpart to the biological sample. If the suspected substance is present, the resulting immunochemical reaction can be demonstrated by precipitation of the reaction complex (for example, an antibody-antigen complex). This reaction complex is generally difficult to detect visually. For this reason, either antibodies or antigens are often bound to insoluble particles, for example polymer latex particles, so that when the complex is formed, it is readily detectable from the resulting agglutination by observing either the presence of clumping or a detectable tracer associated with the particles. Agglutination then is characterized by the clumping of particles from a suspension of particles. Further details of known agglutination methods are provided in U.S. Pat. Nos. 4,419,453 (issued Dec. 6, 1983 to Dorman et al) and 4,459,361 (issued July 10, 1984 to Gefter).

Of the several groups of Streptococci, group A Streptococcus (*S. pyogenes*) is primarily responsible for causing pathological conditions in humans, such as B-hemolytic pneumonia, scarlet fever, rheumatic fever, cardiac sequelae, glomerulonephritis, septic sore throat and puerperal sepsis. Because of the serious nature of infections potentially caused by Streptococcus A, it is important to diagnose its presence in an early stage of infection so that an appropriate course of treatment may be selected. Early tests for detection required culturing a biological sample for long periods of time, usually at least 18 and up to 48 hours. In most cases, such lengthy tests undesirably delay treatment.

More recent agglutination tests for Streptococcus A have been described which are allegedly quicker than the culturing techniques (see, for example, U.S. Pat. No. 4,618,576, issued Oct. 21, 1986 to Rosenstein et al, and E.P. Publication Nos. 150,567 and 174,195).

Nonspecific interactions between latex particles which cause them to agglutinate are normally controlled through electrostatic repulsion. In other words, sufficient similar charges are present on the particles to repel other particles. However, problems have arisen in agglutination assays for a number of immunoreactive species [for example, Streptococcus A, human chorionic gonadotropin (hCG), Chlamydia, Gonorrhea, herpes, HTLV, HIV-I (formerly known as LAV or HTLV-III virus) and others]. When certain proteins (for example, receptors for an immunoreactive species to be determined) are attached to the particles, the resulting net charge is a mixture of positive and negative charges. This leads to significant nonspecific interactions among the particles as well as increased nonspecific interactions between the particles and other charged surfaces in the environment, for example, microporous membranes. It would be desirable to significantly reduce or eliminate all of these nonspecific interactions in order to increase assay sensitivity.

SUMMARY OF THE INVENTION

The problems noted above have been overcome with an immunoreactive reagent useful in the determination of an immunoreactive species, the reagent comprising water-insoluble particles having tracer molecules associated therewith, and having bound to the outer surfaces of the particles:

(i) receptor molecules reactive with the species, and
(ii) molecules of a protein having a pI less than about 6, which protein is not reactive with either the species or the receptor molecules wherein the weight ratio of the receptor molecules to the protein molecules is from about 100:1 to about 1:10.

This invention also provides a method for the preparation of the immunoreactive reagent described above comprising:

providing a suspension of water-insoluble particles having tracer molecules associated therewith, and substantially simultaneously, contacting the particles with (i) receptor molecules reactive with the species, and
(ii) molecules of a protein having a pI less than about 6, which protein is not reactive with either the species or the receptor molecules so as to attach the receptor molecules and the protein molecules to the outer surfaces of the particles, the protein being present in an amount such that substantially all of it is attached to the particles and the resulting weight ratio of the receptor molecules to the protein molecules is from about 100:1 to about 1:10.

A method for the determination of an immunoreactive species in an aqueous liquid comprises:

(a) contacting the liquid with the immunoreactive reagent described above so as to form a reaction product of the species and the receptor molecules, (b) separating the reaction product from unreacted immunoreactive reagent, and (c) determining the amount of tracer either in the reaction product or the unreacted reagent.

Use of the reagent of this invention provides an assay of significantly improved sensitivity because nonspecific interactions among particles and between particles and other charged materials nearby are greatly reduced. These results are achieved by immobilizing one or more proteins having a relatively low pI onto the particles along with immobilized receptor molecules. These proteins are reactive with neither the receptor molecules nor the immunoreactive species which is being determined in the assay.

It is important that the weight ratio of receptor molecules and low pI protein molecules be from about 100:1 to about 1:10 in order to maximize assay sensitivity and reduce nonspecific interactions. If too much protein is immobilized, there is too little receptor on the particle surface to detect low amounts of species. If too little protein is immobilized, the nonspecific interactions are unacceptably high. It should be noted that U.S. Pat. No. 4,459,361, noted above, describes an agglutination assay for penicillin G in Example 1, wherein penicillin G, conjugated to bovine serum albumin, is adsorbed onto latex beads. The resulting agglutination reagent comprises conjugate (5.5:1 conjugate to bovine serum albumin) in addition to a solution of unconjugated bovine serum albumin (9.6 mg/ml). Bovine serum albumin was included in the immobilization medium in excess in order to block undesired protein adsorption and to act as a stabilizer in the medium to keep the beads from agglutinating prematurely. The presence of a large amount of bovine serum albumin is a considerable waste of material and would cause additional intereference in the assay of species present in a test sample at low concentration.

Further improvements in reducing nonspecific interactions among particles can be achieved by adding negative charge to the receptor molecules with a modifying agent. For example, this can be done by either acylating, alkylating or sulfonylating the receptor molecules as described in more detail below.

In a preferred embodiment of this invention, the reagent is useful in an agglutination assay whereby reaction of the immobilized receptor molecules with the immunoreactive species forms a detectable agglutinate.

BRIEF DESCRIPTION OF THE DRAWING

The FIGURE is a graphical plot of log (relative background fluorescence) vs. the amount of succinic anhydride used to acylate antibodies attached to polymeric particles as described in Example 2 below.

DETAILED DESCRIPTION OF THE INVENTION

The present invention provides a diagnostic test for an immunoreactive species which can be performed in a very short time without the use of complicated equipment. This permits the test to be performed in a doctor's office or at home and enables the doctor or consumer to determine the presence of an analyte based upon the results of the test the same day. The test detects the presence of the species in a biological sample, such as a swab specimen from the throat, urine specimen or sample of another aqueous liquid. Such biological samples can be tested with or without pretreatment (for example, filtration) to remove unwanted debris or interferents.

The method of this invention can be used to detect and quantify any of a wide variety of immunoreactive species. Such species are generally proteins, hormones, carbohydrates, or lipopolysaccharides which have one or more sites for complexing with a corresponding receptor, for example, corresponding antibodies for antigens. Alternatively, the species to be detected can be an antibody which has one or more complexing sites reactive with the corresponding antigen or an anti-antibody. Immunoreactive species which can be detected with this invention include, but are not limited to, Streptococcus A antigen, antigens from chlamydial and gonoccocal organisms, retroviral antigens or antibodies (HIV or HTLV), human chorionic gonadotropin (hCG), leutinizing hormone (LH), herpes viruses, drugs, antibiotics, and other hormonal, bacterial or viral antigens and antibodies. In some instances, the species must be extracted from the organism or virus found in the biological specimen. In other instances, the species is already in reactive form and requires no extraction procedures prior to the assay. Extraction procedures for a given species are known to one skilled in the art. Exemplary extraction procedures for Streptococcus A antigen are described below.

Preferably, the invention is used to detect a multivalent immunoreactive species, such as Streptococcus A antigen as is demonstrated in the following embodiment and in Example 1 below. This embodiment of the invention relating to Streptococcus A antigen is presented for illustrative purposes, but it will be understood that the scope of this invention is not so limited. A biological sample suspected of containing the antigen can be collected from a patient in any suitable manner. However, generally an applicator means is used to collect a biological sample by contacting the area of suspected infection with the applicator swab thereby collecting cells of Streptococcus A organisms if they are present. Subsequently, the antigens are extracted from the organisms in a suitable manner. A preferred extraction procedure includes dipping the swab in a suitable extraction composition containing one or more reagents which singly or in combination cause release of the Streptococcus A antigen from the organism, specimen cells and other debris in the sample.

Useful extraction compositions known in the art include a mixture of nitrite salt and glacial acetic acid, as described in E.P. Publication No. 150,567, and enzymes derived from the bacterium *Streptomyces albus* as described in U.S. Pat. No. 4,618,576, noted above. A preferred extraction composition is a mixture of a nitrite salt (for example, sodium nitrite or potassium nitrite) with an organic acid (for example, succinic or citric acid), as described in copending and commonly assigned U.S. Ser. No. 098,431, filed on even date herewith by Snyder et al and entitled KIT FOR EXTRACTING STREPTOCOCCUS A ANTIGEN AND A METHOD OF USING EXTRACTED ANTIGEN, abandoned.

Extraction can be accompanied by incubation for a short period of time if desired. Centrifugation can also be used to remove extraneous material. After extraction, the medium containing the extracted antigen can be neutralized if necessary to bring the medium pH to that appropriate for antigen-antibody reaction. See for example, Slifkin et al, *J. Clin. Microbiol.* 15(1), pp. 187–189, 1982.

The presence of an immunoreactive species, for example, Streptococcus A antigen, is detected by the immunoreactive reagent of this invention which comprises water-insoluble particles having tracer molecules associated therewith and receptor molecules (for example, antibodies to Streptococcus A antigen) reactive with the species bound in a suitable manner to the surface of the particles. Reaction (or immunochemical binding) between immunoreactive species and receptor then results in a reactive product which can be detected in a suitable manner. For example, the reaction product can be further reacted with another receptor which complexes with the immunoreactive species. This second receptor can be the same or different from that immobilized on the particles. It can be labeled or unlabeled. Preferably, the complex forms large agglutinates which can be detected. Alternatively, the unreacted materials can be detected in a suitable manner.

Suitable particles useful as part of the immunoreactive reagent can be natural or synthetic particles which are water-insoluble and capable of having a suitable number of tracer molecules associated therewith in some manner. Examples of useful particles include ferritin crystals, agarose particles, glass beads, polymeric particles, such as latex particles, and others known in the art. The following references describe representative useful particles: U.S. Pat. Nos. 3,700,609 (issued Oct. 24, 1972 to Tregear et al), 3,853,987 (issued Dec. 10, 1974 to Dreyer), 4,108,972 (issued Aug. 22, 1978 to Dreyer), 4,401,765 (issued Aug. 30, 1983 to Craig et al), 4,419,453 (issued Dec. 6, 1983 to Dorman et al), 4,459,361 (noted above), 4,478,946 (issued Oct. 23, 1984 to Van der Merwe) and 4,591,571 (issued May 27, 1986 to Kuboyama et al). The particles useful in this invention are generally quite small, that is less than about 2 micrometer in diameter. Preferably, they have an average diameter of from about 0.1 to about 1 micrometer.

Particularly useful particles are polymeric latex particles, and more preferably they are what are known in the art as core-shell polymeric latex particles. A wide variety of monomers can be used in the preparation of such particles as long as the particles are water-insoluble. A worker skilled in the polymer chemistry art would be able to design and prepare suitable latex particles. Preferred core-shell polymeric latex particles in the practice of this invention are described in Examples 3 and 5 below. These particles have a core composed of homo- or copolymers of styrene, and a shell composed of homo- or copolymers of chloromethylstyrene or (2-chloroethylsulfonylmethyl)styrene.

The particles useful in the practice of this invention have sufficient tracer molecules associated therewith in order to allow quantitative determination of the species from the amount of tracer seen in either the reaction product or in the unreacted residual materials. The tracer molecules are preferably distributed within the particles. Any tracer material which allows detection can be used. If ferritin crystals are used as the particles, the tracer molecules are molecules of iron inherently in those crystals. Other natural or synthetic particles can have, as tracers: radioisotopes, colorimetric compounds, fluorescent compounds, chemiluminescent compounds, phosphorescent compounds and other detectable materials known in the art. Preferably, the tracer is a radioisotope, colorimetric dye or fluorescent compound (for example, a dye or rare earth chelate). A worker skilled in the art would be able to combine an appropriate tracer with the particular particle used.

In one embodiment, the tracer can be a fluorescent rare earth chelate such as an europium chelate, as described for example, in U.S. Pat. No. 4,259,313 (issued Mar. 31, 1981 to Frank et al). In another and preferred embodiment, the tracer is a colorimetric compound which is readily detected in the agglutinate. Useful dyes are known in the art. Some dyes can be incorporated into the particles when the particles are prepared. Alternatively, the dyes are imbibed into preformed particles in such a manner that they do not leach out.

The tracer can be distributed within the particles in any suitable manner. For example, the tracer can be uniformly distributed therein as shown for example in U.S. Pat. No. 3,853,987 (noted above). Preferably, the tracer molecules are located in a restricted area of the particles, for example, near the surface or predominantly in the interior thereof. In the preferred core-shell particles, the tracer can be in either the core or shell, but most preferably, it is substantially in the core of the particles. In other words, very little (for example, less than 5% by weight) of the dye is in the shell portion of the particles.

Receptor molecules (for example, antibodies) reactive to the immunoreactive species to be detected, such as Streptococcus A antigen, are bound to the outer surfaces of the particles in a suitable manner, for example by adsorption or covalent attachment. Attachment can be achieved using known techniques, as described for example in the references cited above. Covalent attachment is preferred as the receptor molecules are less likely to be removed from the particles after attachment. When covalently attached, the receptor molecules can be bound directly to the particles or through suitable linking groups. When the receptor molecules are antibodies, either monoclonal or polyclonal antibodies can be used, but monoclonal antibodies (whole or fragments) are generally preferred. Antibodies can be obtained commercially or prepared using known techniques.

The receptor molecules are preferably chemically modified with a suitable modifying agent which is capable of adding negative charge to the molecules. Examples of such modifying agents include acylating agents, alkylating agents, sulfonylating agents, oxidizing and reducing agents, electrophilic agents as described in *Enzyme-Immunoassay*, Maggio (Ed.), CRC Press, Inc., Boca Raton, Fla., 1980, pp. 72–77. The receptor molecules are modified after attachment to the water-insoluble particles.

Representative useful acylating agents are described in U.S. Pat. No. 5,591,571 (noted above) with anhydrides such as succinic anhydride being most preferred. Alkylating agents, such as chloroacetic acid, chloropropionic acid, fluoronitrobenzene, bromoacetic acid, bromomalonic acid and bromopropionic acid are also useful with bromoacetic acid being most preferred. Useful sulfonylating agents include m-(chlorosulfonyl)benzoic acid and p-(chlorosulfonyl)benzoic acid.

Also bound to the outer surfaces of the particles are molecules of one or more proteins, each of which has a pI less than about 6. None of these proteins is reactive with either the species to be detected or the receptor molecules which are also bound to the particles. The term pI (that is, isoelectric point), is known as the pH at which the number of positive and negative charges are equal. The pI value of a protein can be measured using conventional equipment and procedures. For example, it can be measured by isoelectric focusing using a suitable isoelectric focusing plate, such as a LKB Ampholine PAG plate (available from LKB-Produkter AB, Bromma, Sweden), pH range 3.5–9.5, and standard calibrators.

Particles partially covered with the low pI protein molecules have significantly less attraction to each other. Useful proteins which are within the scope of this invention include casein, succinylated collagen, succinylated casein and succinylated bovine serum albumin. Preferred proteins include casein and succinylated casein. The proteins are bound to the particles in any suitable manner including absorption, covalent attachment and other techniques known to one skilled in the art.

The weight ratio of the receptor molecules to the low pI protein molecules bound to the particles is from about 100:1 to about 1:10, and preferably, the ratio is from about 20:1 to about 1:1.

The immunoreactive reagent of this invention is prepared by contacting suitable water-insoluble particles with the receptor molecules and low pI protein at substantially the same time under conditions which will provide attachment of both materials to the particles. This may mean the presence of reagents which facilitate covalent or adsorptive attachment, suitable pH, temperature, mixing or agitation and other conditions. The amount of protein in the reaction suspension is closely controlled such that substantially all of it is attached to the particles and very little of it remains in the suspension after attachment. This amount will be varied depending upon the surface area of the particles to be covered (that is, the percent solids of the particle suspension and the particle size distribution). The details of a procedure for making the reagent are provided in Example 1 below. Generally, the low pI protein is present in the reaction suspension in an amount of about 0.1 mg/ml or less.

Once a reaction product, for example, an agglutinate, has been formed, the reaction product, for example, agglutinated materials, is separated from unreacted materials, for example, unagglutinated materials in any suitable manner known in the art. Following separation, the amount of tracer is determined in either the reacted or unreacted materials using known procedures. More details regarding these steps are described below.

Simultaneously or subsequent to contact of immunoreactive species with receptor molecules to form the reaction product, the reaction product can also be contacted with a microporous water-insoluble membrane to effect separation in the case of an agglutination reaction. In one embodiment, the agglutinate can be formed in a separate container and then brought into contact with the membrane. Alternatively and preferably, the agglutinate is formed in the presence of the membrane. This membrane (described in detail below) can be simply a filter means held by hand through which unagglutinated materials are filtered. Preferably, however, it is mounted in a test device in which the assay is carried out. Such a test device is also described below.

Any microporous water-insoluble membrane can be used as long as it is inert to the materials used in the assay, and has the desired porosity which will allow fluids and unreacted materials to pass through but which will retain the reaction product. In other words, the membrane pores must be large enough to allow passage of the unagglutinated particles, but not large enough to allow agglutinated particles to pass through. More particularly, the average pore size of the membrane must be at least five times the average diameter of the water-insoluble particles described above. Preferably, the average pore size is from about 6 to about 15 times the average particle diameter. Useful membranes include polymeric materials which are commercially available from various sources, such as Pall Corp (Glen Cove, N.Y.). One useful membrane is a nylon-66 microporous membrane manufactured and marketed by that company as BIODYNE A or ULTIPOR N-66. Further details of useful membranes are provided in copending and commonly assigned U.S. Ser. No. 098,433, filed on even date herewith by Snyder et al and entitled MEMBRANE STRUCTURE COATED WITH LOW pI PROTEIN OR CARBOHYDRATE AND METHODS OF MAKING AND USE.

In an agglutination assay, a suitable incubation period can be used to optimize agglutination, if desired, before or during contact with the membrane. After that period, unagglutinated residual materials are washed through the membrane while leaving the agglutinate thereon. Any suitable wash fluid can be used in this step, but preferably the wash solution has a pH of from about 5 to about 10 and contains an ionic compound, such as salt. Details regarding this preferred wash solution are provided in copending and commonly assigned U.S. Ser. No. 19,850, filed Feb. 27, 1987 by Snyder et al.

Once the unagglutinated residual materials have been washed through the membrane, the amount of immunoreactive species in either the agglutinate or residual materials can generally be determined with the unaided eye if the tracer is a readily viewable colorimetric dye. Otherwise, standard colorimetric detection equipment can be used. Other types of tracers, for example, radioisotopes, fluorescent dyes, phosphorescent dyes, and the like, require suitable detection equipment.

In a preferred embodiment of this invention, a method for detecting Streptococcus A comprises:

(i) providing an applicator including an applicator stick and a fibrous swab and collecting a biological sample with the swab, (ii) providing an extraction composition comprising sodium nitrite and citric acid for effecting release of Streptococcus A antigen from the swab, dipping the swab in the extraction composition and incubating the swab within the extraction composition for a period of time sufficient to release antigen from said swab, (iii) neutralizing the solution of extracted antigen, (iv) contacting the neutralized solution of extracted antigen with the agglutination reagent of this invention so as to form an agglutinate of the reaction product of the antigen and the antibodies, the contacting being carried out in the presence of a microporous water-insoluble membrane mounted in a disposable test device, the membrane having an average pore size which is at least five times the average diameter of the water-insoluble particles described above, (v) washing unagglutinated residual materials through the membrane while leaving the agglutinate thereon, and (vi) determining the amount of tracer in the agglutinate remaining on the membrane.

While the present invention is not so limited, the assay for a multivalent immunoreactive species can be carried out using a suitable test device which comprises the microporous membrane described herein. Such a device can have one or more wells into which extracted antigen is deposited for reaction with the agglutination indicator reagent. This reagent can be added to the device during the assay, or incorporated therein at the time of manufacture. Once the agglutinate is formed, the unagglutinated residual materials can be washed through the membrane with the wash solution into a separate compartment below the membrane. An example of such a test device is described and claimed in copending and commonly assigned U.S. Ser. No. 19,810 filed Feb. 27, 1987 by Hinckley. Other variations of useful test devices would be within the purview of an ordinary worker skilled in the art.

In the examples which follow, illustrating the practice of this invention, the materials used were obtained as follows:

nylon-66 membranes from Pall Corp. (Glen Cove, N.Y.),

Oil Red EGN dye from Aldrich Chemical Co. (Milwaukee, Wis.), succinylated casein was prepared by reacting casein with an equal weight of succinic anhydride for four hours at 25° C., and then purifying the product by dialysis, monoclonal antibodies to the PI antigen of serogroup B of *Neisseria gonorrhea* were obtained using the F62 strain according to the procedure described by Schneider et al in *J. Immun. Meth.*, 54, pp. 101-105, 1982, monoclonal antibodies to Streptococcus A antigen were obtained from Streptococcus A vaccine according to the procedure described by McCarty et al, *J. Exp. Med.*, 102, 11, 1955, monoclonal antibodies to hCG were mouse $IgG_1$ antibodies produced by standard hybridoma technology and had affinities of about $10^9$ molar$^{-1}$, casein, human chorionic gonadotropin and bovine serum albumin from Sigma Chemical Co. (St. Louis, Mo.), carboxymethylcellulose from Hercules, Inc. (Wilmington, Del.), DAI (trademark) Strep A test from Difco Labs (Detroit, Mich.), and the remainder either from Eastman Kodak Co. (Rochester, N.Y.) or prepared using standard starting materials and procedures.

EXAMPLE 1

Agglutination Reagent

This example demonstrates the preparation of an agglutination reagent of this invention and the importance of the low pI protein in reducing nonspecific interactions among polymeric particles.

To prepare the agglutination reagent, latex particles of poly(styrene-co-m,p-chloromethylstyrene-co-2-hydroxyethyl acrylate) (76.2:22.7:1.1 weight ratio) having an average diameter of 0.45 micrometer were used as a suspension of 8% solids in water. A fluorescent europium (III) (thenoyltrifluoroacetone)$_3$ chelate was imbibed into the particles along with trioctylphosphine oxide in the ratio of 1 part chelate to 2 parts oxide according to the procedures described in Belgian Pat. No. 843,647. Solutions of casein and bovine serum albumin were prepared in deionized, distilled water at 10 mg/ml. Borate buffer (pH 8.5, 50 millimolar) was used in the immobilization procedure.

Various ratios of antibodies to protein (casein or bovine serum albumin), at 0.1 mg total weight, were added to 0.6 ml of borate buffer. After extensive mixing, the particle suspension (25 μl, 2 mg solids) was added to the buffered solution and the resulting suspension was rotated end-over-end for 24 hours at 37° C., centrifuged at 7000 rpm for five minutes and the supernatant discarded. The solids were resuspended in 0.1 molar glycine buffer (pH 8.5) (0.3% solids).

An isolate of *Streptococcus pyogenes* (Group A) was obtained from a local hospital. The antigen was extracted from the organism using the reagents and procedures in the DAI (Trademark) Strep A test. Nylon microporous membranes (5 μm average pore size) were pretreated by incubating them in 0.5% instant nonfat dry milk (containing casein), Tris buffer (50 millimolar, pH 8), sodium chloride (100 millimolar) or 7M carboxymethylcellulose (2%). A sample (10 μl) of each suspension of particles was added to a sample (10 μl) of extracted antigen prepared from a solution containing about $10^7$ colony forming units of organisms. The resulting combined samples were incubated for two minutes and 10 μl of each were placed on a treated microporous filter. The agglutinate on the filter was washed under vacuum with a solution of Tris buffer (100 μl, pH 8) and sodium chloride (100 millimolar). Signal-to-background surface fluorescence values remaining on the filters were measured using a standard spectrofluorometer equipped with a surface flourescent accessory (excitation at 342 nm, emission at 612 nm).

The results of these tests showed that attaching bovine serum albumin failed to acceptably reduce backgrounds. However, the attachment of casein to the particles significantly reduced backgrounds. A ratio of 4:1 antibody to casein was most preferred because not only was the background significantly reduced, but the high signal due to the antigen-antibody reaction was retained.

Higher levels of casein, that is, up to 1:10 antibody to casein, also reduced background, but some signal reduction was seen. Lower levels of casein, that is, down to 100:1 antibody to casein, also reduced background, but to a lesser extent, with full signal retention.

EXAMPLE 2

Agglutination Reagent Further Acylated

This example is similar to Example 1 but illustrates the further improvement obtained when the antibody molecules are subjected to acylation prior to use in an assay.

The materials used were the same as described in Example 1. Also prepared was a solution of succinic anhydride in dimethylsulfoxide (10 mg/ml).

To borate buffer (0.9 ml) was added a sample of Streptococcus A antibody (0.12 mg) and casein (0.3 mg). After extensive mixing, a sample (41 μl, 3 mg solids) of the suspension of polymer particles was added to the buffer solution and the resulting mixture was rotated end-over-end for 24 hours at 37° C. The mixture was cooled to room temperature and a given amount (up to 300% by weight of antibody) of succinic anhydride was added, followed by end-to-end rotation for four hours at room temperature. The suspension was then centrifuged at 7000 rpm for five minutes, and the supernatant was discarded. Finally, the solids were resuspended in 0.1 molar glycine buffer (pH 8.5) at a concentration of 0.3% solids.

The agglutination reagent thus prepared was evaluated as described in Example 1. The FIGURE shows the dramatic decrease in background found after succinylation of the antibody molecules on the particles. Decreases in absolute signal were negligible and no loss in antigen detection sensitivity was observed. Further, the reproducibility of the reagent preparation was improved.

It is apparent that the immobilization of a low pI protein as demonstrated in Example 1 significantly reduces undesired nonspecific interactions. However, Example 2 demonstrates that further improvement is possible when the immobilized receptor molecules are acylated.

EXAMPLE 3

Determination of Streptococcus A

This example demonstrates the use of the agglutination reagent of this invention in the determination of Streptococcus A antigen. This example as well as the following Examples 4 and 5 are also described in U.S. Ser. No. 19,850 filed Feb. 27, 1987, noted above. These three examples demonstrate both the invention shown and claimed in that application as well as the present invention.

Core-shell polymeric latex particles containing a red dye (Oil Red EGN) in the core were prepared by imbibing the dye into the particles using the technique described in Belgian Pat. No. 843,647. The particles had been prepared using core/shell polymerization techniques. The core of the particles was composed of poly(styrene-co-2-acetoacetoxyethyl methacrylate) (70:30 weight ratio) while the shell was composed of poly(m,p-chloromethylstyrene). The average diameter of the particles was about 0.45 micrometer. Monoclonal antibodies to Streptococcus A antigen together with casein were immobilized on these particles as follows: to 0.6 ml of 50 mmolar borate buffer (pH 8.5) was added 0.1 mg of total protein comprised of a 10:1 mixture of anti-Strep A antibody (2.9 mg/ml solution in phosphate buffered saline solution, known in the art as PBS), and casein (10 mg/ml water). After mixing, 41.5 μl of a 5% suspension of the polymeric latex particles were added (to provide 0.3% solids) and the resulting solution was rotated (end-over-end) for 24 hours at 37° C. to effect covalent attachment of the antibody and casein to the particles to form an agglutination reagent.

A solution of succinic anhydride (10 mg/ml dimethyl sulfoxide) was added to a suspension of the agglutination reagent described above at a weight ratio of 1 part anhydride to 1 part total protein. The resulting suspension was mixed for four hours at 25° C., centrifuged for 5 minutes at 7000 rpm and the resulting pellet was resuspended in 0.1 molar glycine buffer (pH 8.5) to a concentration of 0.3% solids.

Streptococcus A antigen was extracted from an isolate obtained from a local hospital at 25° C. for 1 minute using a solution of equal volumes of sodium nitrite (8 molar) and citric acid (0.2 molar). The solution was then neutralized with an equal volume of 3-(N-morpholino)-propanesulfonic acid buffer (2 molar, pH 7.5) containing ethylenediaminetetraacetic acid (75 mmolar).

A nylon-66 microporous membrane (5 μm average pore size) was incorporated into a test well of a disposable test device like that described and claimed in U.S. Ser. No. 19,810 of Hinckley, noted above, and pretreated by washing with 100 μl of a 2% succinylated casein solution.

A mixture of sodium chloride (80 μl, 1 molar), the agglutination reagent suspension described above (40 μl), and extracted antigen (80 μl) containing about $4.2 \times 10^5$ colony-forming units was added to the test well of the test device containing the membrane, and incubated therein for two minutes at 25° C. The fluid was then allowed to drain into a compartment below the membrane, and the agglutinate on the membrane was washed with 150 μl of a wash fluid (0.25 molar sodium chloride) having an ionic strength of 0.25.

After the washing step, the amount of dye in the agglutinate on the membrane was measured at 540 nm using reflectance measuring equipment. The Williams-Clapper transform (*J. Optical Soc. Am.*, 43, p. 595, 1953) was used to calculate transmission density values. The agglutinate on the membrane was readily observable and had a significantly greater density value than the density of a background control (the difference was 0.148). These data indicate that the agglutination reagent of the present invention was useful for determination of Streptococcus A antigen from a biological sample.

EXAMPLE 4

Determination of Gonorrhea

This example demonstrates the use of the agglutination reagent of the present invention for the determination of gonorrhea. The agglutination reagent used in this example was composed of latex particles comprised of poly(styrene-co-m,p-chloromethylstyrene-co-2-hydroxyethyl acrylate) (76:23:1 weight ratio) into which had been imbibed 5%, by weight, of europium (III) (thenoyltrifluoroacetone)$_3$ along with trioctylphosphine oxide in the ratio of 1 part chelate to 2 parts oxide according to the procedures described in Belgian Pat. No. 843,647. The particles had an average diameter of about 0.45 micrometer.

Monoclonal antibodies to the PI antigen of the serogroup B of *Neisseria gonorrhea* (also known in the art as the PIB antigen) were immobilized on the particles described above as follows: to 1.3 ml of 50 mmolar borate buffer (pH 8.5) was added 0.15 ml of 1.08 mg/ml antibody solution in phosphate buffered saline (PBS). In addition, 0.32 ml of a 1 mg/ml aqueous solution of casein was added in order to immobilize casein on the particles as well. After mixing, 41.5 μl of a 5% suspension of the latex particles described above were added, and the resulting solution was mixed at 37° C. for 24 hours. Succinic anhydride (0.174 ml of 10 mg/ml dimethyl sulfoxide solution) was added, and the resulting solution was mixed at 22° C. for four hours. This solution was then centrifuged for 10 minutes and the resulting pellet was resuspended in 0.1 molar glycine (pH 8.5) to give a mixture containing 0.3% solids of agglutination reagent.

The PIB antigen was extracted from a specimen of *Neisseria gonorrhea* using a mixture of 1% ethanolamine and 10 mmolar ethylenediaminitetraacetic acid, followed by sonication and filtration.

A nylon-66 microporous membrane having an average pore size of 5 micrometers was pretreated by dipping it into a 2% casein solution. A mixture of sodium chloride (50 μl, 6 molar), antigen solution (50 μl) having a specific amount of antigen (nanogram) and the agglutination indicator solution described above (50 μl) was added to a test tube, incubated at 22° C. for 30 minutes, then filtered through the treated microporous membrane. The resulting agglutinate on the membrane was washed with 0.15 μl of 1 molar tricine buffer (pH 8.6). The amount of agglutinate was determined by measuring the amount of fluorescence in the agglutinate using standard surface fluorescence measuring equipment (excitation, 342 nm and emission, 610 nm). A Control solution containing specific amounts of an extract of a different antigen (that is, the PI antigen of the serogroup A of *Neisseria gonorrhea*, or also known as the PIA antigen) was treated in the same manner in order to measure nonspecific interactions with the antibodies to the PIB antigen. Table I below shows the results of these tests. It is clear that the assay of this invention can be used to determine a desired antigen of a specific serogroup of gonorrhea.

TABLE I

| PIB Antigen Concentration (ng) | Relative Fluorescence | |
|---|---|---|
|  | Test | Control |
| 100 | 107 | 32 |
| 10 | 332 | 120 |
| 1 | 248 | 73 |

EXAMPLE 5

Assay for Human Chorionic Gonadotropin

This example demonstrates the practice of the present invention for the determination of human chorionic gonadotropin (hCG).

Core/shell polymeric particles were imbibed with Oil Red EGN dye according to known procedures. The particle cores were composed of poly(styrene-co-2-acetoacetoxyethyl methacrylate) (85:15 weight ratio), and the particle shells were composed of poly(m,p-chloromethylstyrene-co-methacrylic acid) (99.8:0.2 weight ratio). The particles had an average diameter of about 0.32 micrometer.

Monoclonal antibodies to two different epitopic sites of hCG were immobilized on these particles as follows: to 0.6 ml of 50 mmolar borate buffer (pH 8.5) were added 0.1 mg of 10:1 mixture of hCG antibodies (2.9 mg/ml phosphate buffered saline solution) and casein (10 mg/ml water). The low pI protein casein (10 mg/ml water) was also added in order to immobilize casein onto the particles as well. After mixing, 41.5 $\mu$l of a 5% suspension of the latex particles described above were added and the resulting suspension was rotated (end-over-end) for 24 hours at 37° C. to effect covalent attachment of the antibodies and casein to the particles to form an agglutination reagent.

A solution of succinic anhydride (10 mg/ml dimethyl sulfoxide) was added to a mixture of the agglutination reagent at a weight ratio of 1 part anhydride to 1 part total protein, and the resulting mixture was mixed for 4 hours at 25° C., centrifuged for 5 minutes at 7000 rpm. The resulting pellet was resuspended in 0.1 molar glycine (pH 8.5) to a concentration of 0.3% solids.

Various amounts of hCG (milli I.U./ml) were added to phosphate buffered saline solutions (0.1 molar sodium phosphate and 0.15 sodium chloride) containing 0.5% bovine serum albumin. A nylon-66 microporous membrane having an average pore size of about 5 micrometers was incorporated into a test well of a disposable test device similar to that described in Example 3 above. This membrane was washed with 2 drops of a 1% aqueous solution of succinylated casein. The hCG concentration in milli I.U. is defined as 5000 milli I.U. being equivalent to 1 microgram of purified hCG.

A mixture of 60 $\mu$l of 4 molar sodium chloride, 1 molar tricine buffer (pH 8.6), 60 $\mu$l of suspension of the agglutination reagent described above and 240 $\mu$l of the hCG solutions described above was added to test tubes, gently mixed and allowed to incubate at 25° C. for 10 minutes. A portion of each solution (300 $\mu$l) was added to the test well containing the membrane and allowed to flow through the membrane. Agglutinate formed on the membrane did not flow through, however. It was washed with 300 $\mu$l of a 1 molar sodium chloride solution, and the amount of dye in the agglutinate was measured at 540 nm as described in Example 3. The results of these measurements are shown in Table II below as transmission density ($D_T$). It indicates that the assay of this invention can be used to determine hCG.

TABLE II

| hCG Antigen (milli I.U./ml) | $D_T$ |
|---|---|
| 0 | 0.043 |
| 500 | 0.047 |
| 1000 | 0.133 |

The invention has been described in detail with particular reference to preferred embodiments thereof, but it will be understood that variations and modifications can be effected within the spirit and scope of the invention.

We claim:

1. An immunoreactive reagent useful in the determination of an immunoreactive species, said reagent comprising water-insoluble particles having tracer molecules associated therewith, and having bound to the outer surfaces of said particles:
   (i) receptor molecules reactive with an immunoreactive species, and
   (ii) molecules of a protein having a pI less than about 6, which protein is not reactive with either said immunoreactive species or said receptor molecules wherein the weight ratio of said receptor molecules to said protein molecules is from about 100:1 to about 1:10, said molecules (i) and (ii) being attached to said particles such that there is substantially no coating of either of said molecules over each other.

2. The reagent of claim 1 wherein said receptor molecules are covalently bound to said particles.

3. The reagent of claim 1 wherein said particles are core-shell polymeric latex particles each containing said tracer molecules in the cores only.

4. The reagent of claim 1 wherein said species is an antigen and said receptor molecules are antibodies reactive thereto.

5. The reagent of claim 1 wherein said species is an antibody and said receptor molecules are antigen molecules reactive thereto.

6. The reagent of claim 1 wherein said receptor molecules have been chemically modified with a modifying agent selected from the group consisting of acylating agents, alkylating agents and sulfonylating agents.

7. The reagent of claim 1 wherein said receptor molecules are antibodies for Streptococcus A antigen.

8. The reagent of claim 1 wherein said low pI protein (ii) is either casein or succinylated casein.

9. A method for the preparation of an immunoreactive reagent for the determination of an immunoreactive species comprising:
   providing a suspension of water-insoluble particles having tracer molecules associated therewith, and substantially simultaneously, contacting said particles with
   (i) receptor molecules reactive with an immunoreactive species, and
   (ii) molecules of a protein having a pI less than about 6, which protein is not reactive with either said immunoreactive species or said receptor molecules
   so as to attach said receptor molecules and said protein molecules to the outer surfaces of said particles, said protein being present in an amount such that substantially all of it is attached to said particles, and the resulting weight ratio of said receptor molecules to said protein molecules is from about 100:1 to about 1:10.

10. The method of claim 9 wherein said protein molecules are present in said suspension in an amount of about 0.1 mg/ml or less.

11. The method of claim 9 wherein said low pI protein (ii) is casein or succinylated casein.

12. The method of claim 9 wherein the weight ratio of said receptor molecules to said protein molecules in said suspension is from about 20:1 to about 1:1.

13. A method for the preparation of an agglutination reagent useful for the determination of an immunoreactive species comprising:
   (a) providing a suspension of water-insoluble particles having tracer molecules associated therewith,
   (b) substantially simultaneously, contacting said particles with
      (i) receptor molecules reactive with an immunoreactive species, and
      (ii) molecules of a protein having a pI less than about 6, which protein is not reactive with either said immunoreactive species or said receptor molecules
   so as to attach said antibodies molecules and said protein molecules to the outer surface of said particles, said protein being present in an amount such that substantially all of it is attached to said particles, and the resulting weight ratio of said receptor molecules to said protein molecules is from about 100:1 to about 1:10, and
   (c) chemically modifying said receptor molecules with a modifying agent which is capable of adding negative charge to said molecules.

14. The method of claim 13 wherein said modifying agent is an acylating agent.

15. The method of claim 13 wherein said low pI protein (ii) is casein or succinylated casein.

16. A method for the determination of an immunoreactive species in an aqueous liquid comprising:
   (a) contacting said liquid with an immunoreactive reagent comprising water-insoluble particles having tracer molecules associated therewith, and having bound to the outer surface of said particles:
      (i) receptor molecules reactive with an immunoreactive species, and
      (ii) molecules of a protein having a pI less than about 6, which protein is reactive with either of said immunoreactive species or said receptor molecules,
   wherein the weight ratio of said receptor molecules to said protein molecules is from about 100:1 to about 1:10,
   said molecules (i) and (ii) being attached to said particles such that there is substantially no coating of either of said molecules over each other,
   so as to form a reaction product of said species and said receptor molecules,
   (b) separating said reaction product from unreacted materials, and
   (c) determining the amount of tracer either in said reaction product or said unreacted materials.

17. The method of claim 16 for the determination of Streptococcus A antigen in a biological sample.

18. The method of claim 16 wherein said contacting step (a) is carried out in the presence of a microporous water-insoluble membrane, and said reaction product is kept on said membrane while said unreacted materials are washed through said membrane.

19. The method of claim 16 which is an agglutination assay.

20. An immunoreactive reagent useful in the determination of an immunoreactive species, said reagent comprising water-insoluble particles having tracer molecules associated therewith, and having bound to the outer surfaces of said particles:
   (i) receptor molecules reactive with an immunoreactive species, and
   (ii) molecules of a protein having a pI less than about 6, which protein is not reactive with either said immunoreactive species or said receptor molecules
   wherein the weight ratio of said receptor molecules to said protein molecules is from about 100:1 to about 1:10,
   said reagent having been prepared by contacting said particles with said receptor molecules and with said protein molecules substantially simultaneously.

* * * * *